United States Patent
Ogura (10) Patent No.: US 9,269,534 B2
(45) Date of Patent: Feb. 23, 2016

(54) SAMPLE HOLDER AND METHOD FOR OBSERVING ELECTRON MICROSCOPIC IMAGE

(71) Applicants: NATIONAL INSTITUTE OF ADVANCED INDUSTRIAL SCIENCE AND TECHNOLOGY, Chiyoda-ku (JP); LIFESEM INC., Suginami-ku (JP)

(72) Inventor: Toshihiko Ogura, Ibaraki (JP)

(73) Assignees: NATIONAL INSTITUTE OF ADVANCED INDUSTRIAL SCIENCE AND TECHNOLOGY, Chiyoda-ku (JP); LIFESEM INC., Suginami-ku (JP)

( * ) Notice: Subject to any disclaimer, the term of this patent is extended or adjusted under 35 U.S.C. 154(b) by 0 days.

(21) Appl. No.: 14/416,848

(22) PCT Filed: Jun. 12, 2013

(86) PCT No.: PCT/JP2013/003701
§ 371 (c)(1),
(2) Date: Jan. 23, 2015

(87) PCT Pub. No.: WO2014/017008
PCT Pub. Date: Jan. 30, 2014

(65) Prior Publication Data
US 2015/0214003 A1    Jul. 30, 2015

(30) Foreign Application Priority Data
Jul. 23, 2012  (JP) ................ 2012-162925

(51) Int. Cl.
*H01J 37/26* (2006.01)
*H01J 37/28* (2006.01)
*H01J 37/20* (2006.01)
*G01N 23/225* (2006.01)

(52) U.S. Cl.
CPC ............ *H01J 37/261* (2013.01); *G01N 23/225* (2013.01); *H01J 37/20* (2013.01); *H01J 2237/004* (2013.01); *H01J 2237/003* (2013.01)

(58) Field of Classification Search
USPC .................... 250/306, 307, 309–311, 440.11, 250/441.11, 442.11, 492.1, 492.2, 492.3, 250/526; 73/864.91
See application file for complete search history.

(56) References Cited

U.S. PATENT DOCUMENTS 6,992,300 B2 *  1/2006  Moses ............... H01J 37/20
                                         250/311
7,745,802 B2 *  6/2010  Nishiyama ......... H01J 37/20
                                         250/306

(Continued)

FOREIGN PATENT DOCUMENTS

JP   2002 8960    1/2002
JP   2004 515049  5/2004

(Continued)

OTHER PUBLICATIONS

Ogura, T., "A high contrast method of unstained biological samples under a thin carbon film by scanning electron microscopy", Biochemical and Biophysical Research Communications, vol. 377, pp. 79-84, (2008).

(Continued)

*Primary Examiner* — Bernard E Souw
(74) *Attorney, Agent, or Firm* — Oblon, McClelland, Maier & Neustadt, L.L.P.

(57) ABSTRACT

In an upper main body of a sample holder, a laminate of an insulative thin film and a secondary electron emission protective thin film is provided. An electron beam emitted from an electron gun enters the secondary electron emission protective thin film side. The undersurface of the insulative thin film is a sample adhesion surface, where a sample to be an observation target is held by adsorption or the like. The secondary electron emission protective thin film is made of a material having a low secondary electron emission coefficient δ and, preferably, is non-insulative. That is, the secondary electron emission protective thin film is conductive even though the electric resistance is high. Accordingly, the charge level of a site irradiated with the electron beam has a low charge level.

19 Claims, 7 Drawing Sheets

(56) References Cited

U.S. PATENT DOCUMENTS

| | | | |
|---|---|---|---|
| 2001/0052573 A1 | 12/2001 | Takakuwa | |
| 2004/0046120 A1* | 3/2004 | Moses | H01J 37/20 250/311 |
| 2008/0308731 A1* | 12/2008 | Nishiyama | H01J 37/20 250/310 |
| 2014/0346352 A1* | 11/2014 | Ogura | H01J 37/20 250/307 |

FOREIGN PATENT DOCUMENTS

| | | |
|---|---|---|
| JP | 2008 210765 | 9/2008 |
| JP | 2010 97844 | 4/2010 |
| JP | 2011 7766 | 1/2011 |
| JP | 2013 134952 | 7/2013 |

OTHER PUBLICATIONS

Ogura, T., "Direct observation of the inner structure of unstained atmospheric cells by low-energy electrons", Measurement Science and Technology, vol. 23, 085402, URL:http://iopscience.iop.org, pp. 1-8, (2012).

International Search Report Issued Jul. 16, 2013 in PCT/JP13/003701 Filed Jun. 12, 2013.

* cited by examiner

Ti THIN FILM

FIG.3B

Cr THIN FILM

FIG.3C

INSULATIVE FILM ONLY

SAMPLE HOLDER AND METHOD FOR OBSERVING ELECTRON MICROSCOPIC IMAGE

TECHNICAL FIELD

The present invention relates to a technique for observing an electron microscopic image and, in particular, to a technique suitable for observing an organic material sample and a biological sample that are susceptible to damage due to electron beam irradiation as an electron microscope image that is sharp and has high contrast.

BACKGROUND ART

A scanning electron microscope (SEM) has been widely used not only for morphological observation on an inorganic material sample or an organic material sample but also for observation on a biological sample, and is an apparatus suitable for observing microorganisms, such as bacteria and viruses, which cannot be observed by the unaided eye.

Unfortunately, there are problems in that such a biological sample is susceptible to damage due to electron beam irradiation and it is difficult to acquire a high contrast image. For SEM observation on a biological sample, typically, a sample as an observation target is pretreated; in this pretreatment, the sample is fixed with formaldehyde or the like, the surface of which is coated with gold, platinum, carbon or the like or stained with heavy metal or the like. This pretreatment is elaborated to reduce the damage from the electron beam to the sample while improving the contrast.

Recently, a method has also been developed that acquires a high contrast image without the aforementioned coating or staining on a biological sample (see Patent Literature 1 and Non Patent Literature 1). In this method, an observation target sample is attached to the undersurface (back surface) of a thin sample supporting film (carbon film), and irradiated with an electron beam accelerated onto the top surface (front surface) of the sample supporting film at a relatively low voltage. The electron beam incident on the sample supporting film is diffused and spreads in the supporting film. Electrons, reaching the undersurface of the supporting film and therearound, cause secondary electrons to be emitted. The secondary electrons are absorbed by the observation target sample attached to the undersurface of the supporting film to thereby provide contrast, which enables a sharp SEM image to be acquired.

The energy of such secondary electrons is significantly low, which is about 10 eV. The electrons cause almost no damage even if being absorbed by a biological sample. Furthermore, the degree of absorption of the electron beam as it is represented as contrast. Accordingly, a significantly clear and high contrast SEM image can be acquired. Such an observation condition is referred to as an "indirect secondary electron contrast condition".

The method has further advanced, and methods have been developed that form a conductive thin film under an insulative thin film, and use a charging effect resulting from incidence of an electron beam to further improve resolution and contrast (see Patent Literature 2 and Non-Patent Literature 2).

CITATION LIST

Patent Literature

Patent Literature 1: Japanese Patent Laid-Open No. 2010-097844

Patent Literature 2: Description of Japanese Patent Application No. 2011-286018

Non Patent Literature

Non Patent Literature 1: T. Ogura, "A high contrast method of unstained biological samples under a thin carbon film by scanning electron microscopy", Biochem. Biophys. Res. Commun. Vol. 377, pp. 79-84 (2008)

Non Patent Literature 2: T. Ogura, "Direct observation of the inner structure of unstained atmospheric cells by low-energy electrons", Meas. Sci. Technol. Vol. 23, 085402(8pp) (2012)

SUMMARY OF INVENTION

Technical Problem

As described above, conventionally, for SEM observation on a biological sample which is susceptible to damage due to irradiation with an electron beam and of which high contrast image is difficult to be acquired, treatment, such as surface coating or staining, is performed. Unfortunately, such treatment requires experience and skill; furthermore, a chemical agent used for staining is often a hazardous substance, such as uranyl acetate, which is unfavorable in view of environment.

The problem of an SEM image observed in the indirect secondary electron contrast condition is that it has significantly high contrast but has relatively low resolution. Furthermore, secondary electrons with low energy accelerated in an ordinary condition cannot pass through the interior of an observation sample. Such a scheme is unsuitable for inner structure observation.

Meanwhile, in the aforementioned methods that form the conductive thin film under the insulative thin film and use the charging effect resulting from incidence of the electron beam, observation with a biological sample attached to the undersurface of the insulative thin film reduces resolution owing to secondary electron scattering.

This is because the conductive thin film becomes at the ground potential, the charging effect resulting from electron beam irradiation causes secondary electrons to pass from the insulative thin film to the conductive thin film, and no potential gradient is formed at a position where the biological sample is held. This phenomenon becomes more significant in the case where a biological sample is sealed in a sample holder at the atmospheric pressure and observed. Furthermore, at an upper portion of the insulative thin film, a large amount of secondary electrons are generated due to charging, which is also a cause to reduce the contrast of an image.

An object of the present invention, which has been made in view of such problems, is to provide a sample holder and a method of observing an electron microscopic image using the same that allow significant easy observation at high resolution and high contrast at the atmospheric pressure without staining a biological sample or the like, and can significantly reduce damage due to an electron beam in observation through a scanning electron microscope.

Solution to Problem

In order to solve the aforementioned problems, a sample holder according to the present invention is a sample holder used for observing an electron microscopic image, including: a laminate of a secondary electron emission protective thin film having a low secondary electron emission coefficient δ and an insulative thin film, the laminate having an electronbeam-incident surface on a side of the secondary electron emission protective thin film and a sample adhesion surface on a side of the insulative thin film; and a conductive thin film facing but being separated from the insulative thin film, wherein a potential of the conductive thin film can be controlled to a same potential as a ground potential of an electron microscope or to a plus potential.

Preferably, the secondary electron emission protective thin film is non-insulative.

For instance, the secondary electron emission protective thin film principally contains any of titanium, carbon, aluminum, and silicon.

Moreover, the thickness of the secondary electron emission protective thin film is, for instance, 30 nm or less.

Preferably, the insulative thin film principally contains any of silicon nitride, silicon oxide, Kapton, and polyimide.

For instance, the insulative thin film has a thickness of 200 nm or less.

Preferably, the conductive thin film principally contains any of nickel, titanium, aluminum, gold, silver, copper, cobalt, molybdenum, tantalum, tungsten, and osmium.

For instance, the conductive thin film has a thickness of 30 nm or less.

The sample holder according to the present invention may be an embodiment where metal particles are attached to a surface of the secondary electron emission protective thin film on an electron-beam-incident side.

In this case, preferably, the metal particles have a diameter of 10 μm or less.

Moreover, the sample holder according to the present invention may be an embodiment where a metal pattern is provided on the electron-beam-incident surface of the secondary electron emission protective thin film or the sample adhesion surface of the insulative thin film.

In this case, preferably, the metal pattern has a line width of 10 μm or less.

Furthermore, the sample holder according to the present invention may be an embodiment where the sample adhesion surface of the insulative thin film is subjected to hydrophilic treatment. Alternatively, the sample holder may be an embodiment where sample absorbent is provided on the sample adhesion surface of the insulative thin film.

In this case, preferably, water absorbent may be provided at an end of the sample adhesion surface of the insulative thin film.

The sample holder according to the present invention may be, for instance, an embodiment where the insulative thin film and the conductive thin film are separated by a spacer having a height of 200 μm or less.

Moreover, the sample holder according to the present invention may be an embodiment where a field stop having an opening with a diameter substantially identical to a diameter of a region on which an electron beam is incident and which is irradiated with the beam is provided on a side of the electron-beam-incident surface of the secondary electron emission protective thin film.

A method of observing an electron microscopic image according to the present invention is a method of observing an electron microscopic image using the sample holder according to the present invention wherein an acceleration voltage of an electron beam is set to a value at which 50% or more of incident electrons are absorbed in or shielded by the laminate, and the electron-beam-incident surface is scanned with the electron beam.

Moreover, the method of observing an electron microscopic image according to the present invention may be an embodiment where liquid is dropped on the sample adhesion surface of the insulative thin film, and an observation sample is held by the liquid.

Advantageous Effects of Invention

The secondary electron emission protective thin film provided for the sample holder according to the present invention has conductivity even though the electric resistance is high. Accordingly, the charge level at a site irradiated with the electron beam is low, and the charging effect resulting from the aforementioned irradiation with electron beam is reduced, which prevents secondary electrons generated in the surface layer of the secondary electron emission protective thin film from released out of the film to reduce the contrast of the image.

On the contrary, the insulative thin film is charged by incident electrons, and the interior of the film has a minus potential. An observation sample, such as a biological sample, is held on the undersurface of this insulative thin film. The conductive thin film is provided facing the sample. If the conductive thin film is controlled to have the same potential as the ground potential of the electron microscope or a plus potential, a potential gradient occurs between the insulative thin film and the conductive thin film, and secondary electrons having passed through the interior of the biological sample move along the potential gradient. Accordingly, the electrons become resistant to be scattered in the interior of the sample, and the resolution is improved.

Moreover, most of the incident electron beams are scattered or absorbed in the laminate of the secondary electron emission protective thin film and the insulative thin film, and the damage to the observation sample due to the electron beam is significantly reduced.

Furthermore, in the case of adopting the embodiment of applying hydrophilic treatment to the sample adhesion surface of the insulative thin film and dropping the liquid (aqueous solution, etc.) as the sample absorbent on the sample adhesion surface of the insulative thin film to hold the observation sample, biological samples, such as cells, bacteria, and viruses can be observed in a living state. The sample absorbent is not limited to liquid (aqueous solution). Alternatively, the material and the like thereof may be appropriately replaced according to the sample to be observed.

DESCRIPTION OF EMBODIMENTS

Hereinafter, referring to the drawings, a sample holder and a method of observing an electron microscopic image using the same are described.

Figure 1:
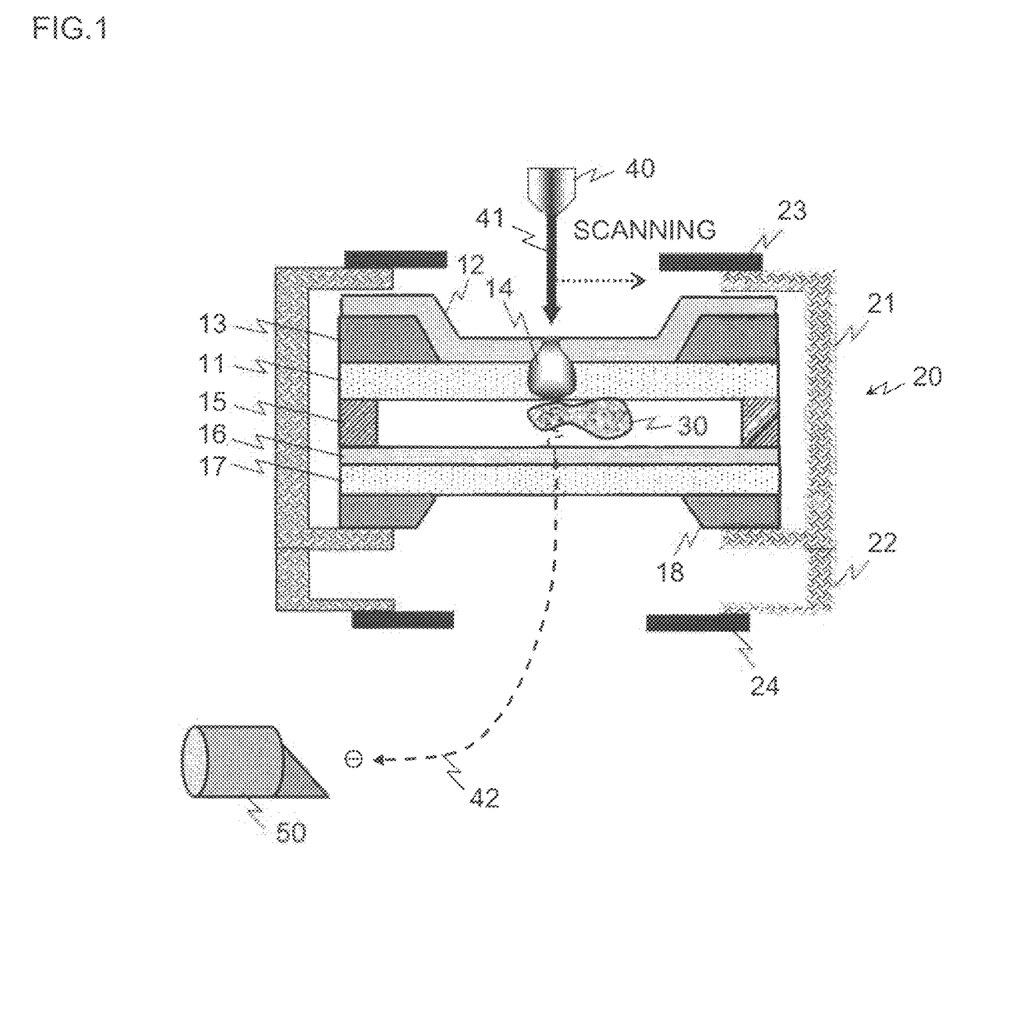
FIG. 1 is a block diagram for illustrating an overview of a configuration example of a sample holder according to the present invention.

FIG. 1 is a block diagram for illustrating an overview of a configuration example of a sample holder according to the present invention. In the example shown in this diagram, the sample holder 20 includes an upper main body 21 and a lower main body 22. In the upper main body 21, a laminate of an insulative thin film 11 and a secondary electron emission protective thin film 12 is provided. An electron beam 41 emitted from an electron gun 40 enters the secondary electron emission protective thin film side. The undersurface of the insulative thin film 11 is a sample adhesion surface, where a sample 30 to be an observation target is held by adsorption or the like. What is indicated by signs 13 and 18 are frames for securing the mechanical strength of the sample holder 20.

The secondary electron emission protective thin film 12 is made of a material having a low secondary electron emission coefficient δ and, preferably, is non-insulative. That is, the secondary electron emission protective thin film 12 is conductive even though the electric resistance is high. Accordingly, the charge level of a site irradiated with the electron beam has a low charge level. As a result, the charging effect by the electron beam irradiation is reduced, secondary electrons generated in a surface layer of the secondary electron emission protective thin film 12 become resistant to be emitted out of the film, and reduction of contrast of the image due to secondary electron emission is suppressed.

The material of such a secondary electron emission protective thin film 12 may be exemplified as a material principally containing any of titanium, carbon, aluminum, and silicon. The thickness of the secondary electron emission protective thin film 12 is, for instance, 30 nm or less.

Preferably, the acceleration voltage of the electron beam is set to a value allowing at least 50% of incident electrons to be absorbed or shielded by the interior of the laminate of the insulative thin film 11 and the secondary electron emission protective thin film 12, and the electron-beam-incident surface is scanned with the electron beam. A two-dimensional SEM image through an intensity profile acquired by a secondary electron detector 50 detecting secondary electrons 42 having passed through the sample 30.

The incident electron beam 41 is diffused and spreads in the insulative thin film 11 (diffusion region 14), and reaches the undersurface (sample adhesion surface) of the insulative thin film 11 while generating secondary electrons. When the electron beam 41 is incident, the potential of the insulative thin film 11 becomes a negative potential according to the amount of electron injection owing to the insulation of the insulative thin film 11.

A conductive thin film 16 having pressure resistance is provided facing but separated from the insulative thin film 11 via a spacer 15. The interior of this separation is sealed by the insulative thin film 11 and the conductive thin film 16, thereby enabling the inner pressure to be held at the atmospheric pressure. The height of the spacer 15, i.e., the interval between the insulative thin film 11 and the conductive thin film 16 is configured to, for instance, 200 μm or less.

The material of the insulative thin film 11 may be exemplified as a material principally containing any of silicon nitride, silicon oxide, Kapton, and polyimides. The thickness of the insulative thin film 11 is configured to be, for instance, 200 nm or less.

Moreover, the material of the conductive thin film 16 may be exemplified as a material principally containing any of nickel, titanium, aluminum, gold, silver, copper, cobalt, molybdenum, tantalum, tungsten, and osmium. The thickness of the conductive thin film 16 is, for instance, 30 nm or less.

Additionally, in the embodiment shown in FIG. 1, a pressure-resistant thin film 17 is provided on an undersurface side in order to secure pressure resistance of the conductive thin film 16.

The potential of the conductive thin film 16 can be controlled to the same potential as the ground potential of an electron microscope or to a plus potential. As a result, a steep potential gradient is formed with respect to the insulative thin film 11 having a negative potential due to charging. Thus, secondary electrons having passed through the interior of the observation sample 30 move along the potential gradient, and become resistant to be scattered in the sample, thereby allowing the resolution to be improved.

Additionally, control of the potential of the conductive thin film 16 is performed, for instance, by providing the conductive thin film 16 with such as an electrode for controlling the potential and then applying a voltage from the outside, such as a terminal, provided for the sample holder 20.

Moreover, as shown in FIG. 1, a field stop 23 having an opening with a diameter substantially identical to the diameter of a region on which the electron beam is incident and which is irradiated with the beam may be provided at an upper portion of the sample holder 20 (the electron beam incidence side of the secondary electron emission protective thin film), and a field stop 24 may be provided at a lower portion of the sample holder 20 (electron beam emission surface side).

The field stop 23 contributes to preventing secondary electrons released upward out of the electron beam incident site from leaking outside of the sample holder 20. Such secondary electrons do not include information on the sample 30. Accordingly, if the electrons are detected, the image quality is reduced. The field stop 24 is for limiting the viewing angle of secondary electrons emitted from the lower portion of the sample holder 20 and detected by the secondary electron detector 50, and contributes to improvement in resolution of an observed image.

Figure 2A:
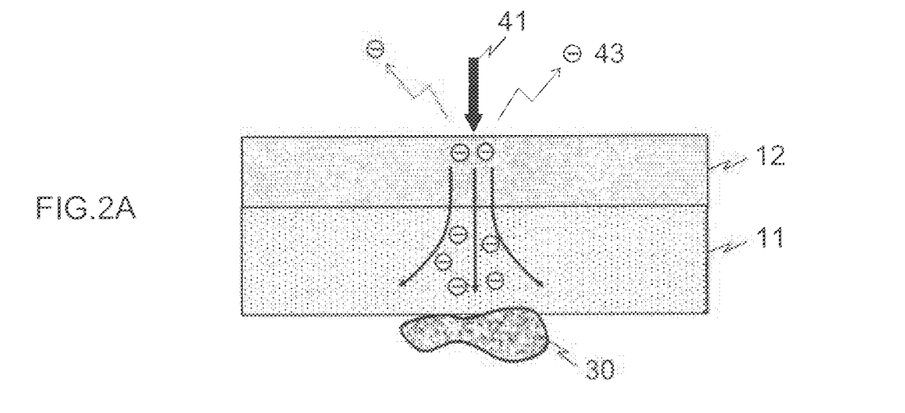
FIG. 2A is a diagram showing a state of secondary electron emission (ejection) during an electron beam being incident on a laminate of an insulative thin film 11 and a secondary electron emission protective thin film 12 having a low secondary electron emission coefficient 6.
Figure 2B:
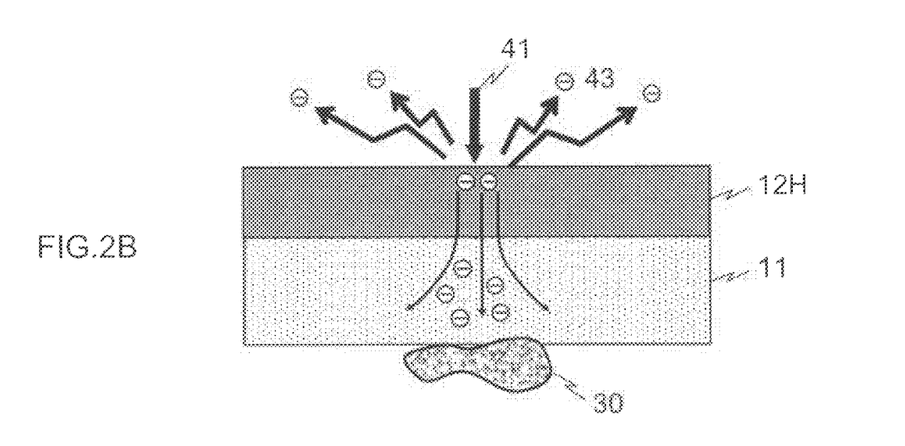
FIG. 2B is a diagram showing a state of secondary electron emission (ejection) during an electron beam being incident on a laminate of an insulative thin film 11 and a thin film 12H having a high secondary electron emission coefficient δ.
Figure 2C:
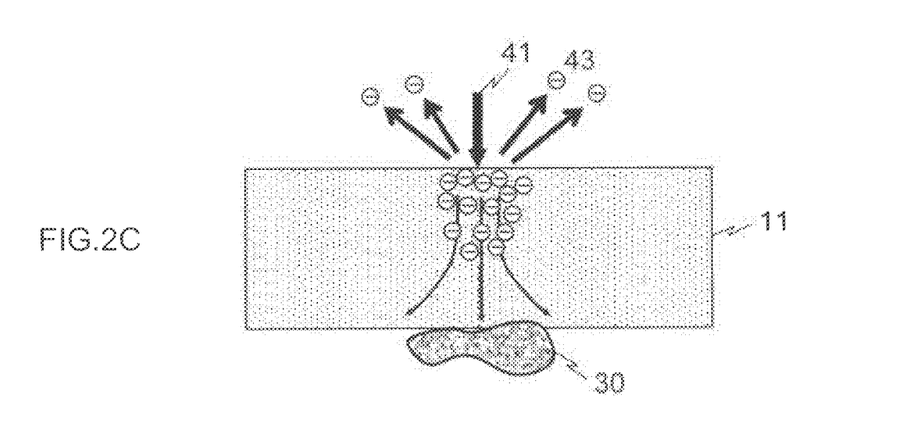
FIG. 2C is a diagram showing a state of secondary electron emission (ejection) during an electron beam being incident on an insulative thin film 11.

FIGS. 2A to 2C are diagrams schematically showing states of secondary electron emission (ejection) during an electron beam being incident. FIG. 2A is a diagram showing the state of secondary electron emission (ejection) during an electron beam being incident on a laminate of an insulative thin film 11 and a secondary electron emission protective thin film 12 having a low secondary electron emission coefficient δ. FIG. 2B is a diagram showing the state of secondary electron emission (ejection) during an electron beam being incident on a laminate of an insulative thin film 11 and the thin film 12H having a high secondary electron emission coefficient δ. In addition, FIG. 2C is a diagram showing the state of secondary electron emission (ejection) during an electron beam being incident on an insulative thin film 11.

In the embodiment shown in FIG. 2A, the secondary electron emission protective thin film 12 having the low secondary electron emission coefficient δ is stacked on the insulative thin film 11. Accordingly, the amount of secondary electrons 43 emitted from the surface layer during incidence of the electron beam 41 is reduced. Moreover, the secondary electron emission protective thin film 12 has a slight conductivity, which keeps low the charge level of the surface level, while suppressing emission of secondary electrons due to charging effect.

Meanwhile, in the embodiment shown in FIG. 2B, the thin film 12H having the high secondary electron emission coefficient δ is stacked on the insulative thin film 11. Accordingly, the amount of emission of the secondary electrons 43 from the surface layer during incidence of the electron beam 41 is large, which is detected by a secondary electron detector and reduces the contrast of the image.

Moreover, in the embodiment shown in FIG. 2C, the electron beam 41 is directly incident on the insulative thin film 11. Accordingly, a large amount of electrons are accumulated in the insulative thin film 11, and the surface has a high negative potential. Therefore, the secondary electrons 43 generated in the surface layer of the insulative thin film 11 are emitted to the outside by Coulomb repulsion, and reduce the contrast of the image.

Figure 3A:
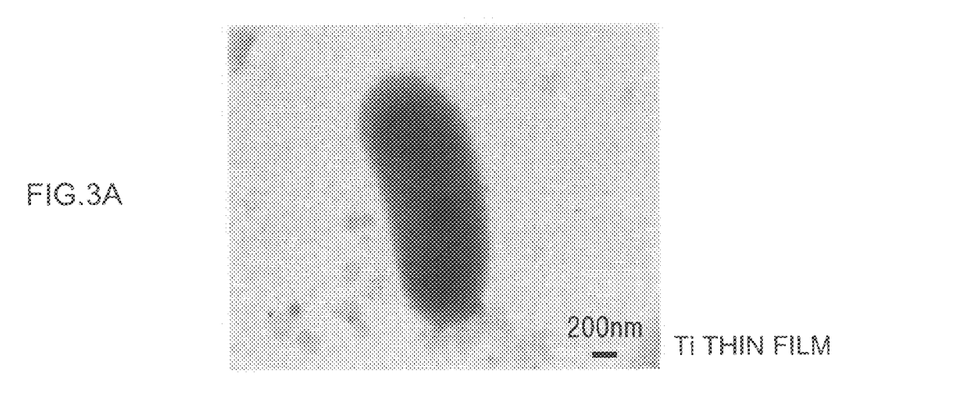
FIG. 3A is a SEM image of a bacterium taken where Ti with a low secondary electron emission coefficient δ is formed as a thin film.
Figure 3B:
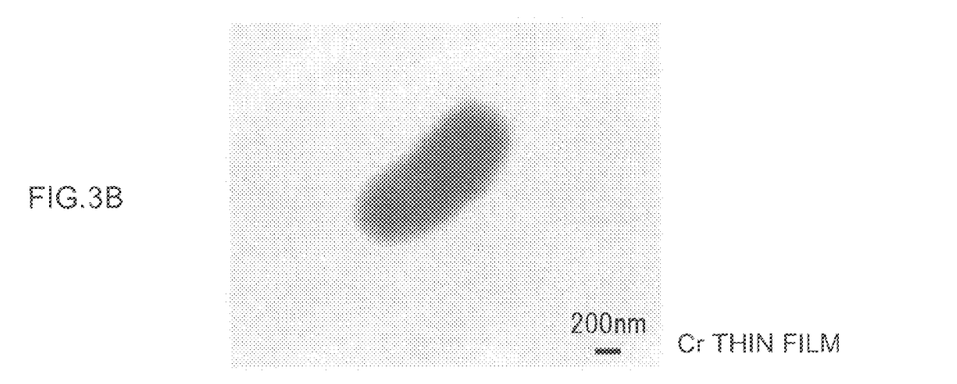
FIG. 3B is a SEM image of a bacterium taken where Cr with a high secondary electron emission coefficient δ is formed as a thin film.
Figure 3C:
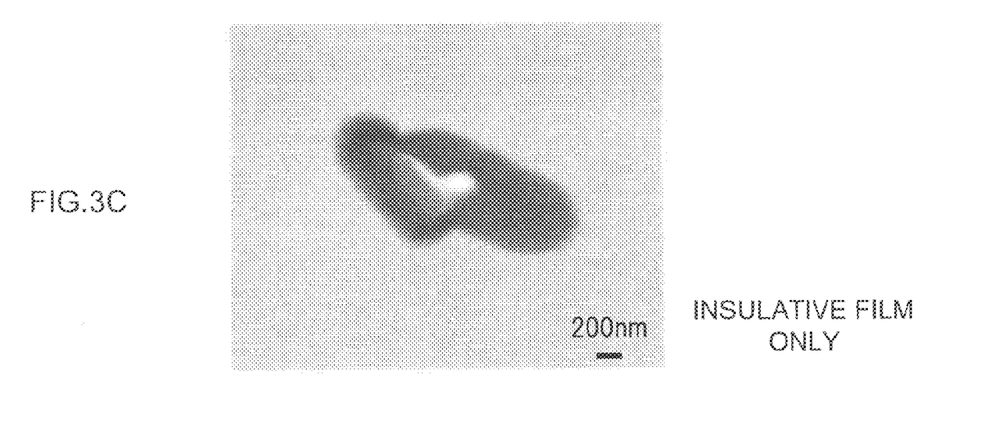
FIG. 3C is a SEM image of a bacterium taken where an electron beam is directly incident on the insulative thin film without forming a thin film.

FIGS. 3A to 3C are SEM images for illustrating effects on the contrast of the image by presence or absence of the thin film to be provided on the insulative thin film 11 and the difference in secondary electron emission coefficient δ of the thin film. These observations are performed using bacteria as samples. Additionally, each of the observation conditions is at an acceleration voltage of 2.6 kV and a magnification of 30,000.

FIG. 3A is a SEM image taken where Ti (secondary electron emission protective thin film) having a low secondary electron emission coefficient δ is formed as a thin film having a thickness of 5 nm. FIG. 3B is a SEM image taken where Cr with a high secondary electron emission coefficient δ is formed as a thin film. FIG. 3C is a SEM image taken where an electron beam is directly incident on an insulative thin film without forming another thin film.

In the case where Ti having a low secondary electron emission coefficient δ is formed as a thin film (FIG. 3A), the amount of secondary electrons released from the surface layer during an electron beam being incident is reduced, and the charge level of the surface layer is kept low. Thus, an image having high contrast can be acquired, thereby allowing the interior of a bacterium and the state of flagella to be sharply observed.

On the contrary, in the case where a Cr thin film (thickness of 5 nm) having a higher secondary electron emission coefficient than that of Ti (FIG. 3B) is formed, the amount of secondary electron emission is large. Accordingly, a whole albescent image is acquired, and the contrast is reduced. As a result, it becomes difficult to observe the interior of the bacterium and the state of flagella.

Moreover, in the case where such a thin film is not formed and the electron beam is directly incident on the insulative thin film (FIG. 3C), charging unevenness as a result of difference in charge level according to the site occurs. Thus, "white patches", which are not in an original structure, are observed at the center of the sample.

Figure 4A:
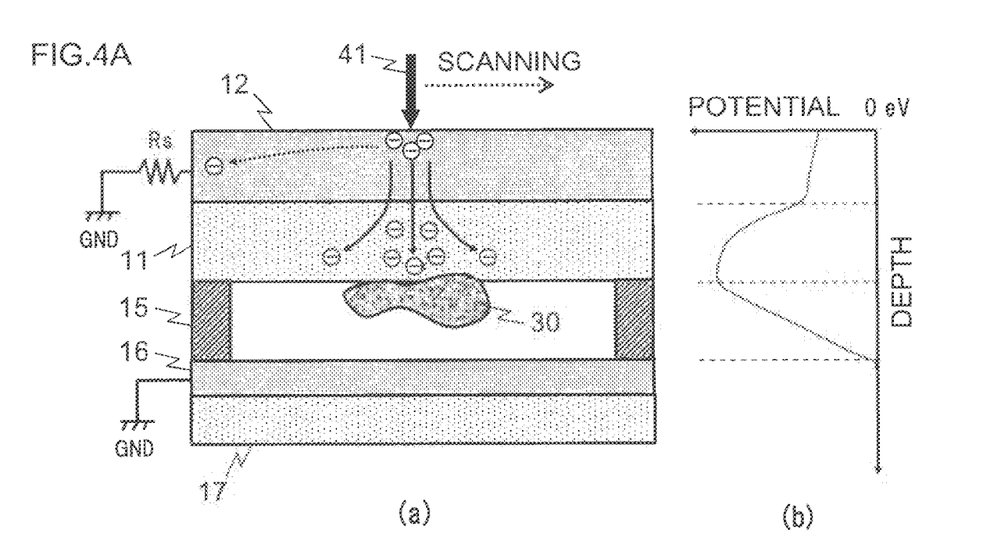
FIG. 4A is a diagram for illustrating effects of a conductive thin film provided facing but separated from the insulative thin film, and showing a state of secondary electrons generated by electron beam incidence.
Figure 4B:
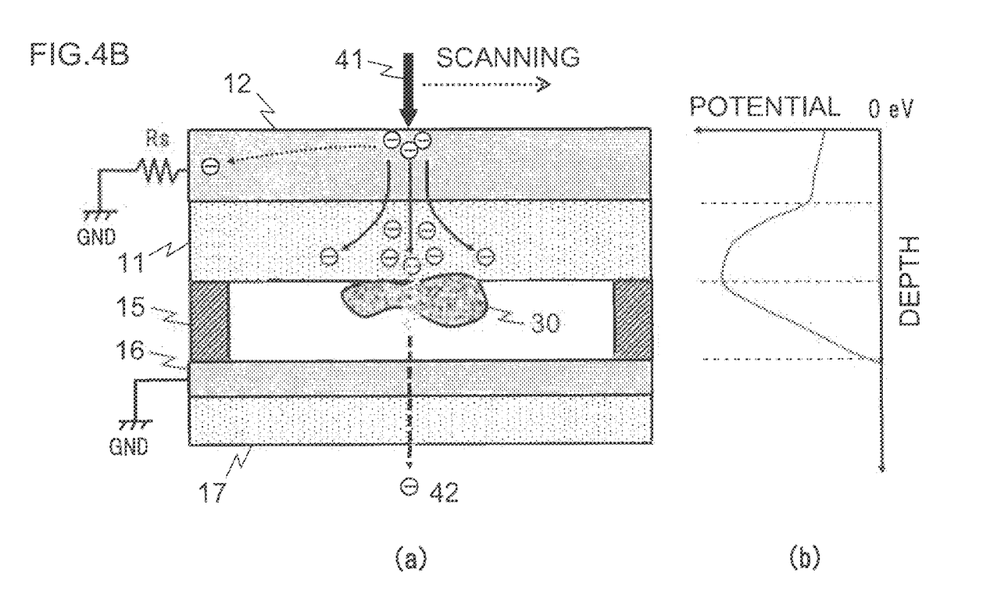
FIG. 4B is a diagram for illustrating effects of a conductive thin film provided facing but separated from the insulative thin film, and showing a state where secondary electrons pass through an observation sample and emitted from a lower portion of the conductive thin film.

FIGS. 4A and 4B are diagrams for illustrating the effects of the conductive thin film 16 provided facing but separated from the insulative thin film 11. FIG. 4A shows a state of secondary electrons generated by electron beam incidence. FIG. 4B shows a state where the secondary electrons pass through the observation sample 30 and are emitted from the lower portion of the conductive thin film 16. Additionally, in the example shown in this diagram, the pressure in the interval between the insulative thin film 11 and the conductive thin film 16 provided via the spacer 15 is set to the atmospheric pressure.

The secondary electron emission protective thin film 12 of such as Ti having a low secondary electron emission coefficient δ is set to the ground potential via a resistor Rs, while the conductive thin film 16 is also set to the ground potential.

When the electron beam 41 is incident, most of secondary electrons generated in the secondary electron emission protective thin film 12 flow into the insulative thin film 11, and the insulative thin film 11 is charged to a negative potential. Thus, a steep potential gradient is formed with respect to the conductive thin film 16 at the ground potential (FIG. 4A). The secondary electrons emitted from the undersurface of the insulative thin film 11 enter the observation sample 30 and move along the potential gradient. Some of the secondary electrons are absorbed in the sample, and the rest of the secondary electrons pass through the sample 30 and are emitted from the undersurface of the conductive thin film 16 (FIG. 4B). The emitted secondary electrons 42 are detected by the secondary electron detector, and form an image. The potential gradient is formed even in the case where the observation sample 30 is a biological sample. Accordingly, the inner structure and the like of the biological sample can be observed at the atmospheric pressure and high contrast and resolution.

Additionally, in the example shown in this diagram, the potential of the conductive thin film 16 is set to the ground potential (0 V). Alternatively, the potential may be set to a plus potential (positive potential).

Figure 5A:
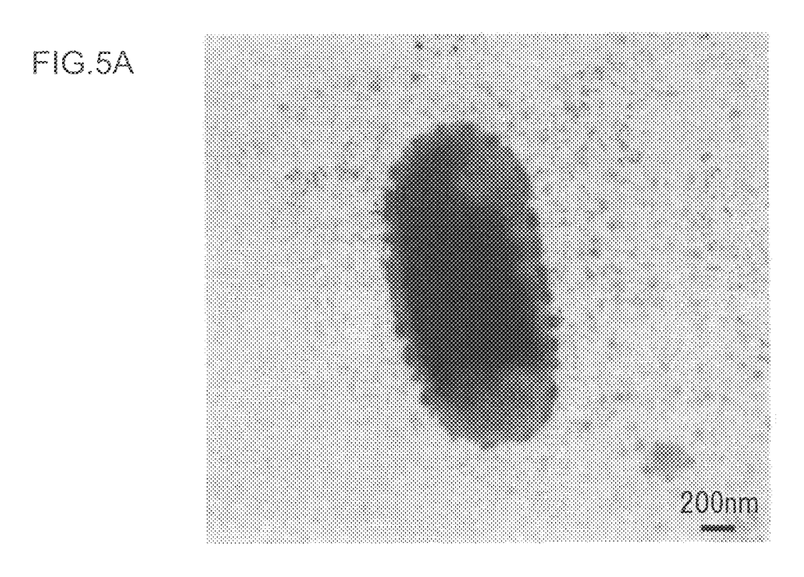
FIG. 5A is a SEM image for illustrating effects on the contrast of an image by presence or absence of the conductive thin film in the case where Ni is formed as a conductive thin film.
Figure 5B:
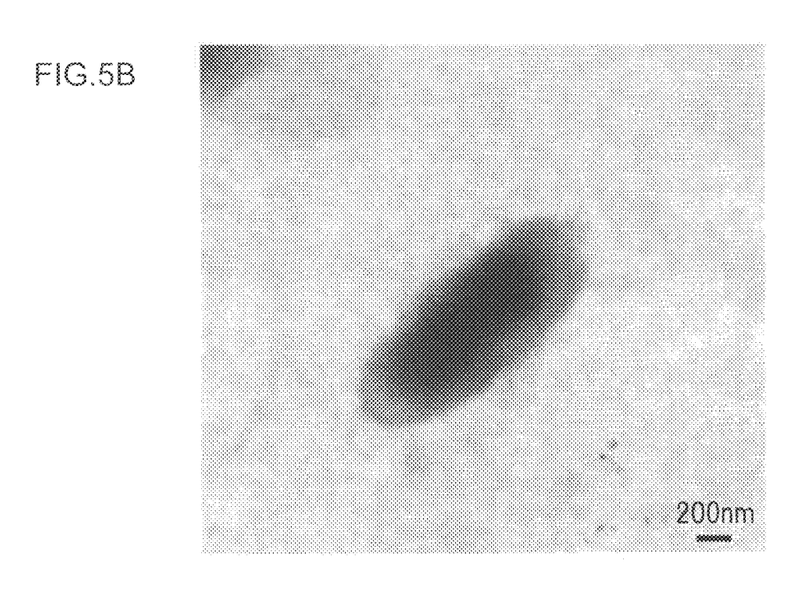
FIG. 5B is a SEM image for illustrating effects on the contrast of an image by presence or absence of the conductive thin film in the case where no conductive thin film is formed.

FIGS. 5A and 5B are SEM images for illustrating effects on the contrast of an image by presence or absence of the conductive thin film 16. These observations are also performed using bacteria as samples. Additionally, each of the observation conditions is at an acceleration voltage of 2.6 kV and a magnification of 30,000.

FIG. 5A shows a SEM image in the case where Ni having a thickness of 5 nm is formed as the conductive thin film 16. FIG. 5B shows a SEM image in the case where the conductive thin film 16 is not formed.

In the case where Ni having a thickness of 5 nm is formed as the conductive thin film 16 (FIG. 5A), the cell wall and the interior of the cell of the bacterium can be significantly clearly observed, and high resolution is confirmed. The image having high resolution is acquired also at high contrast, and the cell wall and the inner state of the bacterium can be sharply observed.

On the contrary, in the case where the conductive thin film 16 is not formed (FIG. 5B), the contrast is significantly reduced, and the image is blurred as a whole. Accordingly, it becomes difficult to observe the cell wall and the interior state.

Figure 6:
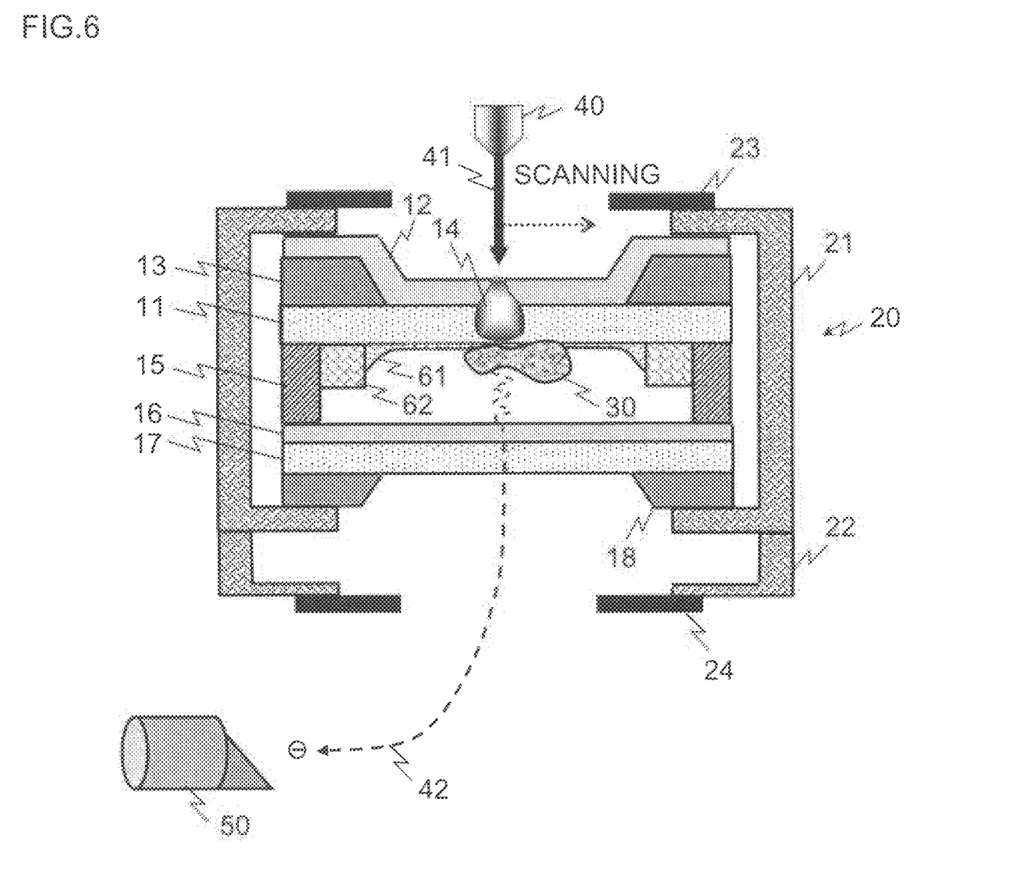
FIG. 6 is a diagram showing an embodiment where hydrophilic treatment is applied to the sample adhesion surface of the insulative thin film, and a SEM image is acquired in a state of a biological sample as an observation sample being held at the atmospheric pressure in a liquid layer formed by dropping liquid (aqueous solution) on the sample adhesion surface.

FIG. 6 is a diagram showing an embodiment where hydrophilic treatment is applied to the sample adhesion surface of the insulative thin film 11, a thin liquid layer of about 100 nm or less as sample absorbent formed by dropping liquid (aqueous solution) 61 on the sample adhesion surface, and a SEM image is acquired in a state of a biological sample as an observation sample 30 being held at the atmospheric pressure in the liquid layer. At the ends of the sample adhesion surface of the insulative thin film 11, water absorbent 62 for preventing the liquid (aqueous solution) from diffusing is provided. This diagram shows the case where the sample absorbent is liquid (aqueous solution). Alternatively, the material and the like thereof may be appropriately replaced according to the sample to be observed.

The biological sample 30 is held in the liquid layer with a part of the sample being soaked. Accordingly, the biological sample 30 being alive can be observed. Additionally, the liquid layer reduces scattering of transmitting secondary electrons, thereby also exerting an effect of improving resolution.

Figure 7A:
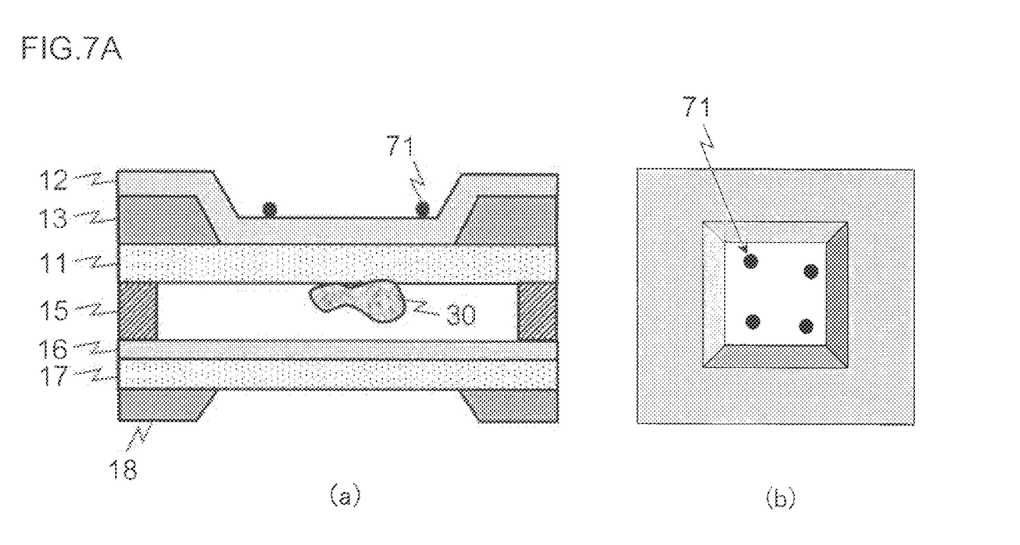
FIG. 7A is a diagram for illustrating an embodiment where metal particles for focus adjustment and the like are provided on the secondary electron emission protective thin film.
Figure 7B:
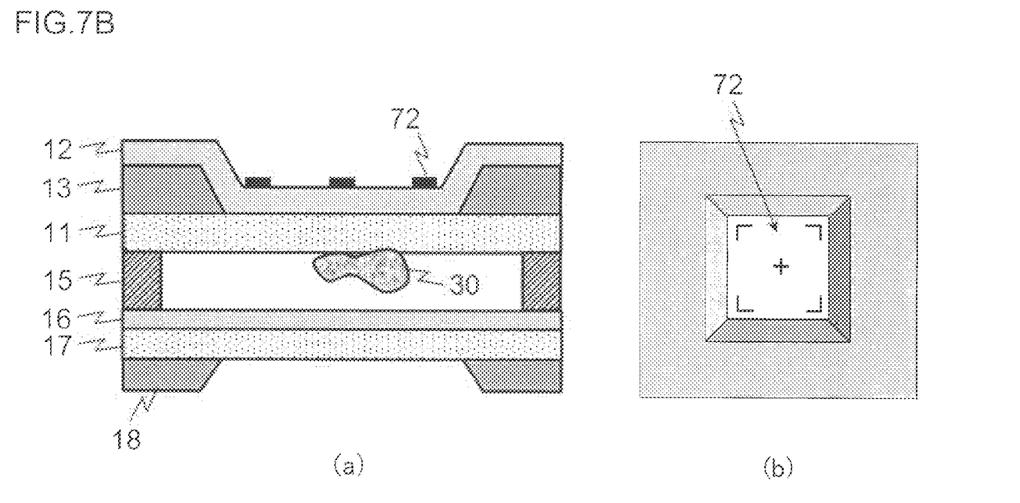
FIG. 7B is a diagram for illustrating an embodiment where a metal pattern for focus adjustment and the like are provided on the secondary electron emission protective thin film.

FIGS. 7A and 7B are diagrams for illustrating embodiments where metal particles 71 (FIG. 7A) and a metal pattern 72 (FIG. 7B) for focus adjustment and the like are provided on secondary electron emission protective thin films 12; (a) shows a sectional view, and (b) shows a top view.

Since the insulative thin film 11 and the secondary electron emission protective thin film 12 are significantly flat, it is difficult to adjust the focus and astigmatism. Accordingly, if the metal particles 71 having a diameter of 10 μm or less or the metal pattern 72 having a line width of 10 μM or less are provided at appropriate intervals, the focus and astigmatism can be easily adjusted.

Additionally, the metal pattern 72 may be provided on the sample adhesion surface of the insulative thin film 11.

INDUSTRIAL APPLICABILITY

As described above, the present invention provides a technique allowing electron microscopic images of an organic material sample and a biological sample, which are susceptible to damage due to electron beam irradiation, to be observed at high resolution and high contrast without treatment, such as surface coating or staining. In particular, the present invention is useful for observing biological samples, such as bacteria, viruses or protein complexes.

REFERENCE SIGNS LIST

11 insulative thin film
12 secondary electron emission protective thin film
12H thin film having a high secondary electron emission coefficient
16 conductive thin film
13, 18 frame
14 diffusion region
15 spacer
17 pressure-resistant thin film
20 sample holder
21 upper main body
22 lower main body
23, 24 field stop
30 sample
40 electron gun
41 electron beam
42, 43 secondary electrons
50 secondary electron detector
61 liquid (aqueous solution)
62 water absorbent
71 metal particles
72 metal pattern

The invention claimed is:

1. A sample holder used for observing an electron microscopic image, comprising:
    a laminate of a secondary electron emission protective thin film and an insulative thin film, the laminate having an electron-beam-incident surface on a side of the secondary electron emission protective thin film having a low secondary electron emission coefficient $\delta$ and a sample adhesion surface on a side of the insulative thin film; and a conductive thin film facing but being separated from the insulative thin film,
    wherein a potential of the conductive thin film can be controlled to a same potential as a ground potential of an electron microscope or to a plus potential.

2. The sample holder according to claim 1, wherein the secondary electron emission protective thin film is non-insulative.

3. The sample holder according to claim 1, wherein the secondary electron emission protective thin film principally contains any of titanium, carbon, aluminum, and silicon.

4. The sample holder according to claim 1, wherein the secondary electron emission protective thin film have a thickness of 30 nm or less.

5. The sample holder according to claim 1, wherein the insulative thin film principally contains any of silicon nitride, silicon oxide, Kapton, and polyimide.

6. The sample holder according to claim 1, wherein the insulative thin film has a thickness of 200 nm or less.

7. The sample holder according to claim 1, wherein the conductive thin film principally contains any of nickel, titanium, aluminum, gold, silver, copper, cobalt, molybdenum, tantalum, tungsten, and osmium.

8. The sample holder according to claim 1, wherein the conductive thin film has a thickness of 30 nm or less.

9. The sample holder according to claim 1, wherein metal particles are attached to a surface of the secondary electron emission protective thin film on an electron-beam-incident side.

10. The sample holder according to claim 9, wherein the metal particles have a diameter of 10 μm or less.

11. The sample holder according to claim 1, wherein a metal pattern is provided on the electron-beam-incident surface of the secondary electron emission protective thin film or the sample adhesion surface of the insulative thin film.

12. The sample holder according to claim 11, wherein the metal pattern has a line width of 10 μm or less.

13. The sample holder according to claim 1, wherein the sample adhesion surface of the insulative thin film is subjected to hydrophilic treatment.

14. The sample holder according to claim 1, wherein a sample absorbent is provided on the sample adhesion surface of the insulative thin film.

15. The sample holder according to claim 13, comprising water absorbent at an end of the sample adhesion surface of the insulative thin film.

16. The sample holder according to claim 1, wherein the insulative thin film and the conductive thin film are separated by a spacer having a height of 200 μm or less.

17. The sample holder according to claim 1, wherein a field stop having an opening with a diameter substantially identical to a diameter of a region on which an electron beam is incident and which is irradiated with the beam is provided on a side of the electron-beam-incident surface of the secondary electron emission protective thin film.

18. A method of observing an electron microscopic image using the sample holder according to claim 1,
   wherein an acceleration voltage of an electron beam is set to a value at which 50% or more of incident electrons are absorbed in or shielded by the laminate, and the electron-beam-incident surface is scanned with the electron beam.

19. A method of observing an electron microscopic image using the sample holder according to claims 13,
   wherein liquid is dropped on the sample adhesion surface of the insulative thin film, and an observation sample is held by the liquid.

\* \* \* \* \*